(12) United States Patent
Hodges et al.

(10) Patent No.: US 6,365,728 B1
(45) Date of Patent: Apr. 2, 2002

(54) REGULATORY ELEMENT FOR EXPRESSING GENES IN PLANTS

(75) Inventors: Thomas K. Hodges, West Lafayette, IN (US); Leszek A. Lyznik, Johnston, IA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/402,328

(22) PCT Filed: Apr. 3, 1998

(86) PCT No.: PCT/US98/06761

§ 371 Date: Nov. 5, 1999

§ 102(e) Date: Nov. 5, 1999

(87) PCT Pub. No.: WO98/44781

PCT Pub. Date: Oct. 15, 1998

Related U.S. Application Data

(60) Provisional application No. 60/042,926, filed on Apr. 4, 1997.

(51) Int. Cl.$^7$ .................. C12N 15/82; C12N 15/29; C12N 5/04; A01H 5/00; A01H 5/10
(52) U.S. Cl. .................. 536/24.1; 435/468; 435/320.1; 435/419; 800/278; 800/298
(58) Field of Search ................... 800/278, 298; 536/24.1; 435/410, 419, 320.1, FOR 160, 161, FOR 147, 192, 468

(56) References Cited

FOREIGN PATENT DOCUMENTS

WO    WO 97/13401    4/1997

OTHER PUBLICATIONS

Doelling, J. H. et al., "The minimal ribosomal RNA gene promoter of *Arabidopsis thaliana* includes a critical element at the transcription initiation site." 1995, The Plant Journal, vol. 8, pp. 683–692.*

Maiti, I. B. et al., "Promoter/leader deletion analysis and plant expression vectors with the figwort mosaic virus (FMV) full length transcript (FLt) promoter containing single or double enhancer domains." 1997, Transgenic Research, vol. 6, pp. 143–156.*

Yoshida, T. et al., GenEmbl, Accession No. D63789, Aug. 07, 1995.*

Fisscher, et al., "Identification of potential regulatory elements in the far–upstream region of the *Arabidopsis thaliana* plastocyanin promoter." Nov. 1994, *Plant Molecular Biology*, vol. 26, No. 3, pp. 873–886.

Dolferus, et al., "Differential Interactions of Promoter Elements in Stress Responses of the Arabidopsis Adh gene." Aug. 1994, *Plant Physiology*, vol. 105, No. 4, pp. 1075–1087.

Lazar, et al., "Identification of Plant Serine–Arginine–Rich Protein Similar to the Mammalian Splicing Factor SF2/ASF." Aug. 1995, *Proc. Natl. Acad. Sci. USA*, vol.92, pp. 7672–7676.

Lopato, et al., "Characterization of a Novel Arginine–Serine–Rich Splicing Factor in Arabidopsis." Dec. 1996, *Plant Cell*, vol. 8, No. 12, pp. 2255–2264.

Su, et al., "Arabidopsis ASF–SF2 Transcripts are Alternatively Spliced." Jul. 1997, *Plant Physiology*, vol. 114, No. 3, p. 246.

* cited by examiner

*Primary Examiner*—David T. Fox
*Assistant Examiner*—Anne R Kubelik
(74) *Attorney, Agent, or Firm*—Barnes & Thornburg

(57) ABSTRACT

The present invention is directed to substantially purified nucleic acids having a novel promoter sequence that expresses genes constitutively at a high level in Arabidopsis cells. The present invention is also directed to expression vectors comprising that promoter sequence and plants produced from the in vitro introduction of such expression vectors.

11 Claims, 1 Drawing Sheet

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 5285 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Arabidopsis thaliana (xi) SEQUENCE DESCRIPTION: SEQ ID NO: 1:

```
GAATTCCAGC GTGGAAGAGA CCAGGACAAC AAACAGCGAG TTTGTATAAA GAAGCCCAAC      60

CACCGGGAGG AGTAAGAGAC GAATCCGCCG CGGTGGATGA AGAAGCGGAT GCGGCGGCGG     120

AGGGAGGAAG AGGGAGGAGA TCGGAGATGA CGGTGGGGAT AGCGGAGTAG CACTGAGTTT     180

TACAACAAAC GTTTCGAACA ATTGAGGAGA ATTTGGTGCA GACGCAAGCG AGACGAGCCC     240

AGTTTCTTGG ATCATCTTGG AGCTTGAAGA AGATGTTGAA GACTACGTCT TCTGGTATAC     300

AAGAGAAGAC AGATTCCGCC ATGGATCGCC TTCTTCTCTC TAGGCGGCTC CTTTCTTATC     360

CAAATTCACT TATACTGTTA TGGGTCCGGT ACGCGTAAAC CGGGAATAGT CTTAACTGTT     420

CTTAAGGTGG GTCACAGATT CACTAACACC CACACAAAGG CAAGTAAGTA ATGCGCAACA     480

GCTCTCGAAA ATGACATCGT ACGGACTGAA CTAAAATGTA AAGGGTCCGG GTATCAAAAT     540

GAGTTCAATG CACATGTCTT TTTAGGTTCA TTTATTGTGA ACGTTTTCAA AATTTTAATA     600

TCGAATTGTG AGCTTTTGAA TTAAGTTTGG TATTCGACAG TAATTTTTGA TAGTTCGTTT     660

TAAGCACTAA CTATATTAGC AAGTCATATA AATCAGCTGA GCTTAGCTCA TAAACTGATG     720
```

```
ATGACTGAGT ATATATCATT CCCATGTGCA AACCCAAGCT AATAAGAATG AAATACACAA    780

CTAGTTTTTC AACTTCTCAT ACATAAGAGA GATCATCTTT ATGAGAATCT TCCAACAGAC    840

CCAGCTCTTT TACCTGATAT GAGATGTTTC TTTACCTGTA AAACAGTTGG AAAGAGATTC    900

AGAGAAAGAG TGAGAATGTT CCAAGCAAGT TAAAAGAGT GTGCATTACC GAGATGGACT    960

CCTGCTTCTG CTCTTGCTCC TACCACGGAT AGGGCTCAGC TGCTTGCTAG GGCTCTTACT   1020

TGCTTCCTTC TGAACCTGCA ACACACACAA TTCAATCCAG ATGATGAGAA TGTAATTAGC   1080

TAGACATAGA TCATGTCTTT TGGATAGTAT GGATTGAAAA CCGAAAATAT TGTGCTGATA   1140

GTATAGCGGA GTAAAAAGTG TATTAGAGAT AGATGACTTA GAGAGGGTAG AGGAGATCTT   1200

GACCTTGAAC GAGATCTGCA AAAGTCCGAG AAACAAATCC AGTTTTAAAA ATCCAATATT   1260

TCCGTGTTTA ATAGCTGTTT CACCAAGACC CTTGATGCCT CATTCCATGT CAGACATCAA   1320

AACACAATCA CAAGAAGCCA AAAGGAAAA AACATATCTT CAGACTATTT TTAGCAGAAA   1380

ATCAAACCAA CACAAGCCTG CTTTTTGTTA AAACAGATGG TAGAGATGGA GAATATCAAA   1440

GCAAATCTAA TTTTATCAAA CCCTGTGTCC AGAACAGCAT CGGTTCCATG AGAATCCAGA   1500

TCGCTTGTCG ATTAGCAGGT AATGAAAATA TCTGTCCTAG CTCGATGGGT CCATTTTGAT   1560

GACACTATAT CAATGCGATC CAATGTCTCT CCACTGTTAC CCATTTAGCA GCAATGGATA   1620

TTATCAGAAA ACGAACTTGC CCATTTAAGA AAGAGCATAT ACCTTTGAGA CGAAACAGTT   1680

GTGTACAACC AACCAAGACA TTCCATGATC CAGATACTAT TTCCCATATT TTAGTTGATT   1740

GTATGTATAT CCATATCTAA GAAACAAAAC CATTCTCAAC ACTATAATTA TAAAAGACCA   1800

GACTTTCAAA GGAAATAAAT CGTGTACCCT TAACTAGAAG CAATCATCAT TCTCAATCAA   1860

CAACTCGGAG TCATCCCAGT GACATCTTTT AATGTGATGT CACCAAACTT CAAGGGAAGA   1920

GCTAAATAGA GCCTATGTTA TGTTTTATGT TGGATATTTT AGCATAAACA TTATAGAAGA   1980

AATGAAGCAT ACCCTCGTGG AGACAGTGAC CTCGACTTAG AGCGGGAGCG AGAGCGAGGA   2040

GATCTCGATG TAGATTTTGC AGGCGATCTA CGCAAAGATT TAGCCTTTGG ACTTCTGCTC   2100

TTGCTCCTGC TTCTGCTGCG GCTACGACTA CGGCTGGGAC TCCGTCCACG GCTGCGGCTC   2160

TTAGAATAGG ATCTTCCACG GCTGGGGCTC CTCGAATCCC TCCTTGAATC ATATTCTCTA   2220

ACCTGTAATG ACATAGGGAA ATGTTAAGTG CAATAAAAAC GAATGCAGCT CTCAGAATTC   2280

TTGTCTTTAA CATACCCGAA CATATTCATG AGAAAACGCA TTCCGAAACT CTGTGTCATC   2340

GAGCTTTTTT TATCTGGACA AAATAAAGAA TATAATCATG AGTAATCAAG GATGAACACA   2400

TTCTCAGCCA CAGTCCCACA CAGAAAATCA AATAATATGA AGAGGAAGAA AAACATCTCA   2460

CCGCATATTT CATGTCCTCG TAGCTGGTAT AATCTACAAT TCCAGTTGTA CCTGTAAATA   2520

AATAGTCCAC GATATAGATT TTTTAAAGCA TGCACAGACT AGTTAAAACA GGATTTAAAG   2580

GCAGAAAACC CAAACAGCTT TAGACACATC TCTATTCTTG GGTAAGACAT GAGGATTTAC   2640

CTCTACCATC ACGAAACACT TGAGAAAAAC AAACTTCTCC TCCTTTACGC ATGTGATCCT   2700

TCAAAACAAA GTGATATGTC AACATTCAGA AATCGTAGAA AATATAGGAA CGACAATGAG   2760

GAATCTGTCC ACAACTGTGT AATCACCTTG AGGTCTTGCC AGGACGCAGA TGAAGGCAAA   2820

CCTGACACTA CAACTGTATA GTGGAAAATC TTAATTTAGT GATTTCTCCT AAAACTTATG   2880

AATACACTAA AGCTAAACAT ATCATATGTA CCGCGGTACT CTGATCTCCT AGATGGTCCA   2940

CGTTCACGAC CACCACCGTC ACCACCACCA CGACCGCCAC GACCACGACC ACTATAACTA   3000

CCGCGTGCAT CATGTGATGA ACGCCTCCCA CCATGAGCTA GTTCCACCTG CAATGGCCAA   3060
```

-continued

```
CACACATAAA TTATGTTTGG CTACCAGTCA ACAATACAAA GTTTGTGTAA AAATTCTGAA    3120

ATTTGATGAT TAACAAACCC GTAAATGATG CCCATCAAAG TCATAACCAT CACGGCCATA    3180

AATTGCATCA TCAGCATCAC GAGCATCCTC AAACTAAATC ACATATATCA CAAAACATTA    3240

GTGGTAGTAT CTCCCAACAT TTGAAAACTC ATGAACACTC AACAACAACG AAGAGCCTAA    3300

CTGTAAAATC AACAACAAGC CTTTATAAAA CATGTGGTTG CATAAAAAAT CTGACCTCGA    3360

CGAATGCATA GCCTGGAGGC CTCGGCGGAA TCTTCAAATC GATTTGAACA ACAGGTCCAT    3420

ACTTCAAAAA AAATAAGGAA GAACAATTCT TAAGGAAACT TCTTCCAAAT AAAATCAGAA    3480

TCCAACAATT CCGAAGATGC ATTCAATTTC TTTCACATGC AAATCTTGTA AAGACATATT    3540

CATCACATAA CACAAAATTC GATCCTGAGT TCTGAGTTCT TAAATTAGGA GAAACGAGTA    3600

ATTTACCTTA CTGAACAAGT CTTCAACTTC TCTTTCACGG ATATCGCCGG GGAAGGTCCC    3660

GACGTAAATC GTTCTACTCG AACGGCTGCT CATTTATTTC TTTCCTATAC CAAAATCAAA    3720

ATTGAGATTC GAAACGTCAA TAGATCGAAA CAAAGAAGCG ATCACACACA AAAAAAACTC    3780

ATTGGATAAC GATTAACCTA AGGAAAACTA AAGAGGTTTG ATTGATCGTC TATATATGAA    3840

CTAAAATTCC AGTAACGATT CCGATCACCT GAGAGAAAAT TCCGATGGAA GAGAAGAAGA    3900

AAGGCGAAAA TTGAAATCTG ACTAGGGCTT TCGAATACCA TAGAGATCAT CACGTGAGTC    3960

ACGTGACCGA CCGGGTACGT ATTAAAATAC ATTGTGTCTT GACCGTATAA AATACATTTG    4020

ACCCGTTTTG CAACAAATCG TAATCTTCAA TCAAAAGCTC TTAAACCCAA AGAACAATT     4080

CCAAATCTTC AATACTTGAT ATTTCTCAAA GAACTTGAAA ACAACACAGA TCCATTCCCA    4140

ATTTCAGATT CACTCAAAAA GGATTTTTCT TTTTTCATTT TCGCTTTTTG TGATCTGGAA    4200

AGTTGTTACC TTTAACAATG TCTCCGAAAC ATCTAGAGTC ATCACGAAGC TCTATTGAAT    4260

CATGCACTTC ACAGCTTCTC TCATGGCGAC CATTTCACCG CTCCAAAACC CTAGACTCAT    4320

CTGACCAACC ACCGCAGACC AATGGGTTTC ACTCCTTTAC TCCCAAACGC CCTTGCTTCT    4380

CCGATCGATC CACTTCTTTC ACCATCGAAG CTATGAGCCG TCTCTCACTC GCCGACGACG    4440

ACAATGGAGG GAAGACATTA TCAGCTTCCA ATTACAGCAA TAGAGGAAGT TTCAGGTTAG    4500

TAGCGAGGAA GCGGCGGCGG CGTAATTCGA GATCGGTGTC TGGTCGGAGT AGTGATCGGA    4560

GTGGGACTCG GAGATGTTGC TCCATTGGTG CTCATGGGAC TTGTTCGGAT TTGCCTTTCG    4620

CTGTTGGTAC AGATTCAAGT GGAGAGCTTT TTGGTGAAGC GAATTGGGCT TCTGATGTGA    4680

GTGAGGCGGC GAGGAATTCA CGGAGAGAGC GGCGAGATTC TGGTGGAGAG AAGGAAGCTT    4740

CTGGTGGATT TGGATTTGCT AATGGAGTTG ATCCAATGGG GAATGAATCT GGGTATGGGA    4800

GTGAGCCTGG TTACAGAGGT GATGCTGAGT TTGGCTATGG TGATGAATTT GATGATGAAG    4860

AAGAAGATGT CGAGCCATTG TTTTGGGGAG GTATTAAATT CAGAGACTTT TTATAGCAAT    4920

TGTGTTCCAT CTTGAGATTC GTGGTTTTTG CTATGAAGAT TTGGAGATTG ATCATCATTG    4980

ATTAGATTAA AGATGACAAC TTTAGTGTTA TTTCTTCTGA TGAAAATGAG TCTGATTTTG    5040

CTCTGCTTGT CTATTATGGC ATTGCCTCAT AGGAATTGTC AGAAAGTTGT CAAATTTGA     5100

TATGTTTAGT GATTGGTGAG TGTTTTGGAT GGAATTGGGT TCTTATCATG TTAGGTCATT    5160

GTCTGAAATG GATATGTATG TACTTGGTAT TTTGATATGT TTAGTGATTG GTGAGTGTTT    5220

TGGATTTGGA GCAGATACAG ATTCCACAAT GGGGATGTCT GGTGAGACAA ATCTCAGATA    5280

GTAAA                                                                5285
```

(2) INFORMATION FOR SEQ ID NO: 2:

(i) SEQUENCE CHARACTERISTICS:
    (A) LENGTH: 530 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

| | | | | | |
|---|---|---|---|---|---|
| CATTTATTTC | TTTCCTATAC | CAAAATCAAA | ATTGAGATTC | GAAACGTCAA | TAGATCGAAA | 60 |
| CAAAGAAGCG | ATCACACACA | AAAAAAACTC | ATTGGATAAC | GATTAACCTA | AGGAAAACTA | 120 |
| AAGAGGTTTG | ATTGATCGTC | TATATATGAA | CTAAAATTCC | AGTAACGATT | CCGATCACCT | 180 |
| GAGAGAAAAT | TCCGATGGAA | GAGAAGAAGA | AAGGCGAAAA | TTGAAATCTG | ACTAGGGCTT | 240 |
| TCGAATACCA | TAGAGATCAT | CACGTGAGTC | ACGTGACCGA | CCGGGTACGT | ATTAAAATAC | 300 |
| ATTGTGTCTT | GACCGTATAA | AATACATTTG | ACCCGTTTTG | CAACAAATCG | TAATCTTCAA | 360 |
| TCAAAAGCTC | TTAAACCCAA | AAGAACAATT | CCAAATCTTC | AATACTTGAT | ATTTCTCAAA | 420 |
| GAACTTGAAA | ACAACACAGA | TCCATTCCCA | ATTTCAGATT | CACTCAAAAA | GGATTTTTCT | 480 |
| TTTTTCATTT | TCGCTTTTTG | TGATCTGGAA | AGTTGTTACC | TTTAACAATG | | 530 |

(2) INFORMATION FOR SEQ ID NO: 3:

(i) SEQUENCE CHARACTERISTICS:
        (A) LENGTH: 530 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

| | | | | | |
|---|---|---|---|---|---|
| CATTGTTAAA | GGTAACAACT | TTCCAGATCT | CAAAAAGCGA | AAATGAAAAA | AGAAAAATCC | 60 |
| TTTTTGAGTG | AATCTGTTAT | TGGGAATGGA | TCTGTGTTGT | TTTCAAGTTC | TTTGAGAAAT | 120 |
| ATCAAGTATT | GAAGATTTGG | AATTGTTCTT | TTGGGTTTAA | GAGCTTTTGA | TTGAAGATTA | 180 |
| CGATTTGTTG | CAAAACGGGT | CAAATGTATT | TTATACGGTC | AAGACACAAT | GTATTTTAAT | 240 |
| ACGTACCCGG | TCGGTCACGT | GACTCACGTG | ATGATCTCTA | TGGTATTCGA | AAGCCCTAGT | 300 |
| CAGATTTCAA | TTTTCGCCTT | TCTTCTTCTC | TTCCATCGGA | ATTTTCTCTC | AGGTGATCGG | 360 |
| AATCGTTACT | GGAATTTTAG | TTCATATATA | GACGATCAAT | CAAACCTCTT | TAGTTTTCCT | 420 |
| TAGGTTAATC | GTTATCCAAT | GAGTTTTTTT | TGTGTGTGAT | CGCTTCTTTG | TTTCGATCTA | 480 |
| TTGACGTTTC | GAATCTCAAT | TTTGATTTTG | GTATAGGAAA | GAAATAAATG | | 530 |

(2) INFORMATION FOR SEQ ID NO: 4:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

```
        (iv) ANTI-SENSE: NO (vi) ORIGINAL SOURCE:
             (A) ORGANISM: Oryza sativa (vii) IMMEDIATE SOURCE:
             (B) CLONE: RTS-1

(xi) SEQUENCE DESCRIPTION: SEQ ID NO: 4:

GAGCCGCCCA CCGATGACGG CGCGGTCCGG GTGGCGGCGG GGCTGACGAA GTGCGTGTCC      60

GGGTGCGGTA GCAAGGTGAC CTCCTGCTTG CTCGGCTGCT ACGGCGGCGG CGGCGGCGCC     120

GCCGCCGCCG CGACGGCGAT GCCGTTCTGC GTCATCGGCT GCACCAGCGA CGTCTTGTCC     180

TGCGCC                                                                186

(2) INFORMATION FOR SEQ ID NO: 5:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

AATAAATGAG CCCGGGTGGT CAGTCCCTTA TGTTACGT                               38

(2) INFORMATION FOR SEQ ID NO: 6:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

TAACAATGTC CCCGGGTGGT CAGTCCCTTA TGTTACGT                               38
```

REGULATORY ELEMENT FOR EXPRESSING GENES IN PLANTS

CROSS-REFERENCES TO RELATED APPLICATIONS

This application is a U.S. national application of international application Ser. No. PCT/US98/06761 filed Apr. 3, 1998, which claims priority to U.S. provisional application Ser. No. 60/042,926 filed Apr. 4, 1997.

FIELD OF THE INVENTION

The present invention is directed to nucleic acid sequences that control the expression of genes in eukaryotic cells. More particularly, the invention is directed to a gene promoter that confers a high level of expression to genes that are operably linked to the promoter.

BACKGROUND AND SUMMARY OF THE INVENTION

The present invention relates to a novel regulatory element which confers a high level of expression in plant cells to genes that are operably linked to the regulatory element. The ability to control the level of gene expression in plants is important for many applications of genetic transformation procedures including those directed to crop improvement.

In eukaryotic organisms, multi-level regulatory systems exist to control gene expression. The transcription process is an integral part of such systems and is involved in synthesis of mRNA molecules. The efficiency of transcription is mostly determined by a region of DNA called the promoter. The promoter consists of gene sequences upstream of the site of transcription initiation. The components of the promoter region include the "TATA" box and often a "CAAT" box. In addition, many other regulatory elements that affect transcription may be present in the promoter sequences. The coordinated action of cellular proteins (transcription factors) interacting with promoter sequences determines the specificity of a particular promoter and its effectiveness. Since most eukaryotic genes are stringently regulated, there is a limited availability of promoters with constitutive, strong expression.

The present invention describes the isolation and purification of a DNA sequence that expresses operably linked genes to high levels in plant cells. The promoter sequence described in the present invention expresses genes at a level equal to or higher than that obtained from one of the strongest presently available promoters —the 35S cauliflower mosaic virus promoter. Such promoters are needed to direct a high level of protein expression in transgenic plants. The strong promoter of the resent invention is used to construct expression vectors for expressing genes in plant cells. In one embodiment, a plant expression vector is provided that comprises the regulatory element of SEQ ID NO: 2 operably linked to a non-natively associated gene, and this vector is used to produce transgenic plants.

DETAILED DESCRIPTION OF THE INVENTION

Definitions

Figure 1:
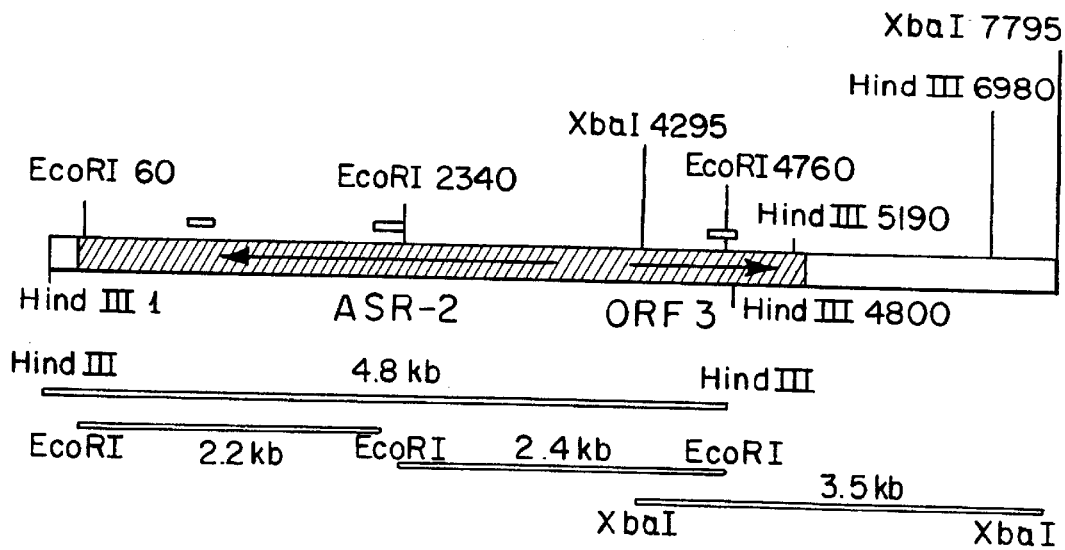
FIG. 1 Represents a restriction map of the 4.8 kb HindIII Arabidopsis genomic fragment that hybridizes to the BglI RTS-1 gene fragment.

Unless specified otherwise, any reference to DNA, a DNA sequence, promoter, or regulatory sequence is a reference to a double stranded DNA sequence. A promoter is a DNA sequence that directs the transcription of a structural gene. Typically, a promoter is located in the 5' region of a gene, proximal to the transcription start site of a structural gene. If a promoter is an inducible promoter, then the rate of transcription increases in response to an inducing agent. In contrast, if the promoter is a constitutive promoter, then the rate of transcription is not regulated by an inducing agent.

An enhancer is a DNA regulatory element that can increase the efficiency of transcription, regardless of the distance or orientation of the enhancer relative to the start site of transcription.

The term "expression" refers to the biosynthesis of a gene product. For example, in the case of a structural gene, expression involves the transcription of the structural gene into messenger RNA and the translation of messenger RNA into one or more polypeptides.

An expression vector is a DNA molecule comprising the regulatory elements necessary for transcription of a gene in a host cell. Typically the gene is placed under the control of certain regulatory elements including constitutive or inducible promoters, tissue-specific regulatory elements, and enhancer elements. Such a gene is said to be "operably linked to" the regulatory elements when the regulating element controls the expression of the gene. Expression vectors typically include eukaryotic and/or bacterial selectable markers that allow for selection of cells containing the expression vector.

An exogenous DNA sequence refers to a DNA sequence that has been introduced into a host cell from an external source. A transgenic plant is a plant having one or more plant cells that contain an exogenous DNA sequence. The term stably transformed refers to a transformed cell or plant that is capable of transmitting an exogenous DNA sequence to its progeny. Typically a stably transformed host has the exogenous DNA sequence integrated into its genome.

A core promoter contains the essential nucleotide sequences for promoter function, including the TATA box and start of transcription. By this definition, a core promoter may or may not have detectable activity in the absence of specific sequences (regulatory elements) that may enhance the activity of the core promoter or confer tissue specific activity.

A visible marker is defined herein as including any gene that encodes a product that produces a phenotypic trait to the host cell or organism.

A selectable marker is defined herein as including any nucleic acid sequence or gene product that can be selected for after introduction into a cell. The selectable marker facilitates the identification of transformants.

A polylinker is a DNA sequence that contains multiple endonuclease restriction enzyme identification sequences in close proximity of one another.

The present invention is directed to a substantially purified genomic DNA sequence isolated from *Arabidopsis thaliana* (SEQ ID NO: 1). The genomic DNA encodes for two proteins (ASR-2 and ORF 3) and contains a dual promoter region located between those two genes that drives the expression of both genes (see FIG. 1).

The genomic region containing the coding DNA sequence for ASR-2, located between nucleotides 945 to 3694 of SEQ ID NO: 1, encompasses sequences that are homologous to a human pre-mRNA splicing factor ASF/SF2 and the Arabidopsis SR1 gene. The alignment of the ASR-2 genomic DNA sequences with the SR1 cDNA sequence indicated the presence of eleven putative exons in the ASR-2 gene, and the deduced amino acid sequence has 82% identity (92% similarity) with the deduced amino acid sequence of SR1. The sequence identity of ASR-2 with the human splicing factor SF2 was 62% as compared to 59% identity between the SR1 and SF2 genes. The ASR-2 gene also appears to have an identical structural organization of RNA-binding domains, the glycine spacer, and the SR domain as is observed in the SR1 and SR2 genes. The ASR-2 coding sequence also includes a highly charged PSK domain at the C-terminal end similar to the SR1 gene but absent in the ASF/SF-2 gene coding sequences.

The regulatory elements controlling the expression of the ASR-2 gene are contained within the 530 nucleotide region shown as SEQ ID NO: 3. The expression of the ASR-2 gene was analyzed by reverse transcription PCR in different parts of Arabidopsis plant. The ASR-2 gene was found to be expressed in all plant parts investigated including the leaves, stems, siliques, and roots. Similar levels of expression were observed in different plant organs. The experiment revealed the presence of more than one transcript hybridizing to the ASR-1 probe (the 2.4 kb EcoRI fragment of ASR-1 genomic clone), and could represent splice variants of ASR-2 transcripts.

The 4.8 kb HindIII genomic fragment encodes for another gene, ORF 3 that is located on the complimentary strand relative to the sequence encoding the ASR-2 gene (see FIG. 1), between nucleotides 4217 and 4917 of SEQ ID NO: 1. A 530 bp region is located between the ASR-2 and ORF 3 genes (at position 3691–4220 of SEQ ID NO: 1) and that 530 bp region functions as a dual promoter for expressing both ASR-2 and ORF 3. The sequence of the DNA region that contains the regulatory elements for expressing ORF 3 is shown as SEQ ID NO: 2.

SEQ ID NO: 2 and SEQ ID NO: 3 are inverse compliments of each other, and accordingly a double stranded DNA sequences that contains SEQ ID NO: 2 will also contain SEQ ID NO: 3. As used herein with reference to double stranded DNA sequences, SEQ ID NO: 2 and SEQ ID NO: 3 will designate the orientation of the 530 bp region in DNA constructs. If the 530 bp region is ligated to a gene through its 3' end (as shown in SEQ ID NO: 1), the sequence will be referred to as SEQ ID NO: 2, and if the 530 bp region is ligated to a gene through its 5' end, the sequence will be referred to as SEQ ID NO: 3. For example, a gene operably linked to a promoter comprising the sequence of SEQ ID NO: 2 designates that the promoter is operably linked to that gene in the orientation naturally expresses the ORF 3 gene.

The 530 bp region located between the ASR-2 and the ORF 3 genes promoter region contains sequences that are known to bind proteins that are involved in the transcriptional process and can function in either direction. Accordingly, this sequence can be used in either orientation as a promoter for expressing genes in eukaryotic cells and more particularly in plant cells. The present invention is directed to a substantially pure DNA sequence comprising the sequence of SEQ ID NO: 2, and the use of such a sequence to express exogenous genes in plants.

In accordance with one embodiment, a recombinant expression vector is prepared comprising a promoter having a consecutive 20 base pair sequence identical to the sequence of SEQ ID NO: 2 or SEQ ID NO: 3. Typically the expression vector will also include a polylinker region located adjacent to the promoter such that upon insertion of a gene sequence into the polylinker, the gene will be operably linked to the promoter. In one embodiment the promoter utilized is the DNA sequence of SEQ ID NO: 2. The expression vector typically includes a eukaryotic selectable marker gene or a visible marker gene to allow identification of plant cells transformed with the exogenous DNA sequence. In one embodiment the expression vector further includes a prokaryotic selectable marker gene and a prokaryotic origin of replication that allow for the transformation and reproduction of the expression vector in prokaryotes.

In accordance with the present invention, a DNA construct comprising the regulatory element of SEQ ID NO: 2, a core promoter and a gene operably linked to the core promoter is used to transform a plant cell, using procedures known to those familiar with the art. Such transformation procedures include but are not limited to microinjection, microprojectile bombardment, electroporation, calcium chloride permeabilization, polyethylene glycol permeabilization, protoplast fusion or bacterial mediated mechanisms such as *Agrobacterium tumefaciens* or *Agrobacterium rhizogenes*.

Transformed cells (those containing the DNA inserted into the host cell's DNA) are selected from untransformed cells through the use of a selectable marker included as part of the introduced DNA sequences. Transformed cells/plant entities can also be identified by the expression of a visible marker included as part of the introduced DNA sequences. Visible markers include genes that impart a visible phenotypic trait such as seed color (i.e., yellow, purple or white genes) or shape (i.e., shrunken or plump genes). Selectable markers include genes that provide antibiotic resistance or herbicide resistance. Cells containing selectable marker genes are capable of surviving in the presence of antibiotic or herbicide concentrations that kill untransformed cells. Examples of selectable marker genes include the bar gene which provides resistance to the herbicide Basta, the nptII gene which confers kanamycin resistance, and the hpt gene which confers hygromycin resistance. An entire plant can be generated from a single transformed plant cell through cell culturing techniques known to those skilled in the art.

In one embodiment a transgenic plant entity is provided wherein the plant entity consists essentially of a plant cell, seed or plant produced from the in vitro introduction of an exogenous nucleic acid sequence into a plant cell, wherein the exogenous nucleic acid sequence encodes a gene whose expression is controlled by the regulatory elements of SEQ ID NO: 2. More particularly, the transgenic plant is generated by transforming a plant cell with a DNA vector comprising a promoter, having a consecutive 20 base pair sequence identical to the sequence of SEQ ID NO: 2 operably linked to a gene. In one embodiment, the DNA vector used to transform the plant cell comprises the 520 bp sequence of SEQ ID NO: 2 operably linked to a gene. The gene may encode for any product that is beneficial to the plant (for example, gene products that directly or indirectly provide herbicide resistance, insecticidal resistance, fungal resistance or act as growth regulators) or may encode for pharmaceutical or polymer components that are subsequently purified from plant material for commercial use. The exogenous nucleic acid sequences used to produce the transgenic plant typically also include a selectable marker gene or a visible marker gene to allow identification of the cells transformed with the exogenous DNA sequence. In accordance with one embodiment, a plant expression vector comprising a regulatory element operably linked to a non-natively associated gene is used to produce a transgenic plant, wherein the regulatory element is selected from the sequence of SEQ ID NO:2.

Figure 2:
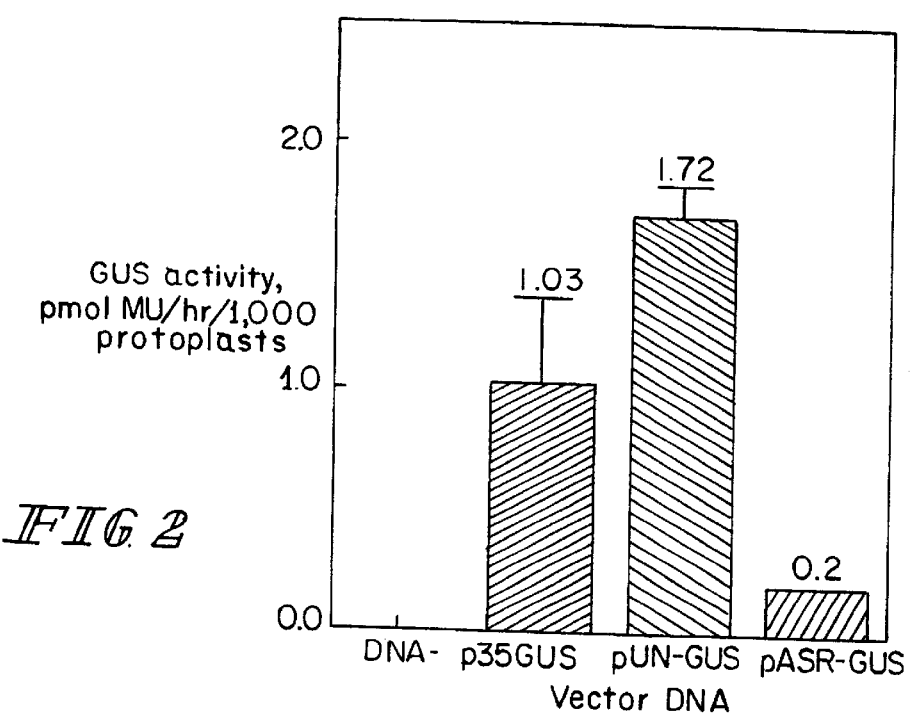
FIG. 2 Expression of gusA in Arabidopsis protoplasts when gusA is operably linked to: the 35S cauliflower mosaic virus promoter (p35GUS), the promoter of SEQ ID NO: 2 (pUN-GUS), the promoter of SEQ ID NO: 3 (pASR-GUS) or lacking a promoter (DNA-).

The regulatory element of SEQ ID NO:2 has been demonstrated to be highly efficient in transcribing genes in Arabidopsis cells (see Example 2 for details). As shown in FIG. 2 the regulatory element of SEQ ID NO: 2 ligated to the gusA coding sequence induced GUS activity at the level of 1.72 nmol MU/hr/1,000 protoplasts, whereas the 35S Cauliflower Mosaic Virus promotor when operably linked to the gusA coding sequence produced GUS activity at 1 nmol MU/hr/1,000 protoplasts. The regulatory element of SEQ ID NO: 3 ligated to the gusA coding sequence exhibited low level of GUS activity in Arabidopsis. Accordingly the 530 bp region, as shown in SEQ ID NO: 2, functions as a strong promoter when operably linked to an exogenous gene in the orientation that naturally expresses the ORF 3 gene in Arabidopsis.

EXAMPLE 1

Isolation of the Genomic Fragment Encoding SEQ ID NO: 1

A genomic library of *Arabidopsis thaliana* ecotype RDL (prepared by ligation of HindIII partially digested genomic DNA fragments, ranging between 8–23 kb, into the HindIII site of the binary cosmid pBIC20) was screened with a BglI fragment of the rice anther-specific cDNA clone RTS-1 (SEQ ID NO: 4) to isolate DNA fragments containing homologous sequences.

The RTS-1 cDNA clone is a tapetum specific gene that encodes an alanine-rich protein that is expressed in tapetum cells of rice anthers. The gene is more fully described in PCT application Ser. No. PCT/US96/16418, published on Apr. 17, 1997 (publication no. WO97/13401), the disclosure of which is expressly incorporated herein.

Library screening was performed in large Petri dishes (20×20 cm) containing approximately 20,000 recombinant colonies of *E. coli* NM554 cells. Such density should represent about three Arabidopsis genome equivalents. The recombinant colonies were lifted on Hybond-N hybridization transfer membranes (Amersham) and membrane-bound DNA (UV irradiation) was probed with the BglI cDNA fragment of the RTS-1 gene (SEQ ID NO: 4). Membranes were prehybridized at 50° C. for 1 hr in pre-hybridization solution containing 5×SSPE, 5×Denhardt's solution, 0.5% SDS, and 0.2 mg/ml denatured salmon-sperm DNA. Hybridization was overnight at 50° C. The filters were washed twice at 50° C. in 3×SSC solution for 15 min, once at 50° C. for 15 min in 1×SSC solution, and in 0.2×SSC solution at 50° C. for 15 min followed by 30 min incubation at room temperature. Washed filters were wrapped in SaranWrap and autoradiography was carried out overnight.

Twenty-three independent clones hybridizing to the probe were identified and selected for endonuclease restriction analysis and Southern blotting. Most of the clones gave rise to multiple signals of varying intensity upon probing with the BglI cDNA fragment of the RTS-1 gene (SEQ ID NO: 4). The initial endonuclease restriction and Southern blot analysis identified genomic clone #2 as having a 4.8 kb HindIII fragment that hybridizes to the RTS-1 probe. This clone was selected for further detailed analysis. When the 4.8 kb HindIII fragment was subsequently restricted into the two 2.2 kb and 2.4 kb EcoRI fragments, both fragments hybridized to the probe indicating two independent probe binding sites.

The 4.8 kb HindIII DNA fragment was sequenced using standard techniques. For sequence analysis, the 2.2 and 2.4 EcoRI fragments internal to the 4.8 kb HindIII fragment (See FIG. 1) were subcloned into the pBluescript KS+/− vector. In addition, DNA fragments generated by digestion of the EcoRI fragments with XbaI were subcloned to facilitate the sequencing process. The sequence of the cross-hatched region shown in FIG. 1 is shown as SEQ ID NO: 1.

A simple homology search for sequences similar to the RTS-1 probe resulted in the identification of three possible binding sites within the 4.8 kb HindIII fragment (indicated as boxes above the cross-hatched region of FIG. 1). The matching percentage was in the range of 35–39% over the 190 bp probe fragment. Experimental results on restriction fragment hybridization to the RTS-1 probe were in agreement with predicted positions of the probe binding sites. The longest open reading frame is located in one region of probe binding and it was selected for further analysis.

A genomic fragment from position 825 to 3694 nucleotide SEQ ID NO: 1 was identified as containing sequences homologous to the human splicing factor ASF/SF2 and the Arabidopsis SR1 gene, and that region was designated as the ASR-2 region (See FIG. 1). The alignment of genomic DNA sequences of this gene with the SR1 cDNA sequences indicated the presence of eleven putative exons with 82% identity (92% similarity) of the deduced amino acid sequences. The sequence identity to the human splicing factor SF2 was 62% as compared to 59% identity between the SR1 and SF2 genes. An identical structural organization of RNA-binding domains, the glycine spacer, and the SR domain was observed among all three genes. The ASR-2 coding sequence also included a highly charged PSK domain at the C-terminal end similar to the SR1 gene but absent in the ASF/SF-2 gene coding sequences.

The presence of ASR-2 transcripts was analyzed by reverse transcription PCR in different parts of Arabidopsis plant. Total RNA was isolated from various Arabidopsis organs and reverse transcription of 5 $\mu$g of the total RNA, treated with RNase-free DNase, was performed with MuMLV-reverse transcriptase (400 units) and oligo dT-$_{18-22}$ primer (4 $\mu$g) for 1 h at 42° C. followed by 5 min at 95° C. Following incubation, the reaction mixture was treated with RNAse H (8 units) for 20 min at 37° C. Five $\mu$l of the reverse transcription reaction was then amplified with Taq-polymerase (Perkin-Elmer Cetus) using primers that recognize the first exon in the RNA recognition domain and the SR domain of ASR-2. Primer sequences were selected that were specific to the ASR-2 domains but not to the SR1 homologous domains.

The ASR-2 gene was found to be expressed in all plant parts investigated including the leaves, stems, siliques, and roots. Similar levels of expression were observed in different plant organs. The experiment revealed the presence of more than one transcript hybridizing to the ASR-2 probe (the 2.4 kb EcoRI fragment of ASR-2 genomic clone). Shorter transcripts were identified in RT-PCR reaction products than expected and could represent splice variants of ASR-2 transcripts. Sequencing of the amplified major RT-PCR product confirmed all predicted intron-exon junction sites except the splicing sites (5' as well as 3') of the intron #7. Such transcripts contain the SR domain message but they cannot be translated into the full length protein because splicing of the intron #7 generates a frame shift mutation leading to a stop codon just after the splice site.

EXAMPLE 2

Expression of gus A using the Promoters of SEQ ID NO: 2 and SEQ ID NO: 3

Arabidopsis protoplasts were transformed with bacterial vectors containing the 5' untranslated ASR-2 DNA sequence connected to the coding sequences of the bacterial b-glucuronidase gene. The coding sequences were ligated to the 3' end and to the 5' end of the promoter sequence and the respective constructs were designated as pUN-GUS [having the promoter orientated in the direction that normally transcribes the ORF-3 gene (i.e., SEQ ID NO: 2) and operably linked to the gusA gene] and pASR-GUS [having the promoter orientated in the direction that normally transcribes the ASR-2 gene (i.e., SEQ ID NO: 3) and operably linked to the gusA gene]. The sequences of the junction site between the promoter sequence and the gusA coding sequence are disclosed as SEQ ID NO: 5 for pASR-GUS and SEQ ID NO: 6 for pUN-GUS wherein the ATG start codon is located at nucleotide 6 and the coding region of the gusA is located at nucleotide 30.

The unique DNA promoter sequence discovered and claimed in the present invention is located between the nucleotides at the position 3690 through 4221, of SEQ ID NO: 1. The sequence is 530 nucleotides in length and is presented as SEQ ID NO: 2 and SEQ ID NO: 3. The 530 bp sequence contains numerous transcription factor binding sites including two "TATA" boxes at positions 141, 316 and "CAAT" boxes located at 223, 386, 448, and 486 and one zeste element (GTGAGTG) at 264 of SEQ ID NO: 2.

The activity of the claimed sequence driving the expression of a foreign gene, gusA, in plant cells was compared to the activity of the 35S cauliflower mosaic virus promotor in Arabidopsis protoplasts. Four expression vectors p35SGUS (having the 35S cauliflower mosaic virus promotor operably linked to the gusA gene), pUN-GUS (as described above), and pASR-GUS (as described above) and a control vector lacking a promoter operably linked to the gusA gene (DNA-), were introduced into the protoplasts by a PEG-mediated transformation procedure. One day after transformation, the GUS activity was determined. The 35S CaMV promotor controlling the gusA sequence produced GUS activity at 1 nmol MU/hr/1,000 protoplasts, while the claimed sequence ligated to the gusA coding through its 3' end (SEQ ID NO: 2) induced GUS activity at the level of 1.72 nmol MU/hr/1,000 protoplasts (see FIG. 2). The claimed sequence ligated to the gusA coding sequence in the opposite orientation (SEQ ID NO: 3) exhibited a low level of GUS activity in Arabidopsis.

What is claimed is:

1. A substantially pure nucleic acid comprising the sequence as set forth in SEQ ID NO:2.

2. A purified regulatory element comprising a nucleic acid comprising the sequence as set forth in SEQ ID NO:2, said regulatory element being capable of regulating gene expression constitutively in an Arabidopsis protoplast at a level equal to or greater than the 35S CaMV promoter.

3. A recombinant expression vector comprising the nucleic acid of claim 2 operably linked to a gene.

4. The expression vector of claim 3, further comprising a gene encoding a eukaryotic selectable marker.

5. The expression vector of claim 4, further comprising nucleic acids having sequences that enable replication of the expression vector in a bacterial host, and a gene encoding a bacterial selectable marker.

6. A plant entity consisting essentially of a plant cell, seed or plant produced from the in vitro introduction of an exogenous nucleic acid of claim 3.

7. An expression vector comprising the nucleic acid of claim 2 and a polylinker sequence.

8. The expression vector of claim 7, further comprising a gene encoding a eukaryotic selectable marker.

9. The expression vector of claim 8, further comprising nucleic acids having sequences that enable replication of the expression vector in a bacterial host, and a gene encoding a bacterial selectable marker.

10. A substantially pure gene construct comprising a first exogenous gene operably linked to a regulatory element wherein the regulatory element comprises the sequence as set forth in SEQ ID NO:2.

11. The gene construct of claim 10 wherein the regulatory element comprises a 3' end and a 5' end, the first exogenous gene is operably linked to the 3' end of the regulatory element, and a second exogenous gene is operably linked to the 5' end of the regulatory element.

* * * * *